United States Patent [19]

Jain

[11] Patent Number: 5,919,147
[45] Date of Patent: Jul. 6, 1999

[54] METHOD AND APPARATUS FOR MEASURING THE VASCULAR DIAMETER OF A VESSEL

[76] Inventor: Krishna M. Jain, 5549 Blue Spruce La., Portage, Mich. 49009

[21] Appl. No.: 08/742,649

[22] Filed: Nov. 1, 1996

[51] Int. Cl.⁶ .................................................. A61B 5/103
[52] U.S. Cl. .......................................... 600/587; 600/481
[58] Field of Search ...................................... 128/774, 897, 128/890; 600/481

[56] References Cited

U.S. PATENT DOCUMENTS

| | | | |
|---|---|---|---|
| 5,010,892 | 4/1991 | Colvin et al. | 128/774 |
| 5,396,887 | 3/1995 | Imran | 128/774 |

FOREIGN PATENT DOCUMENTS

| | | | |
|---|---|---|---|
| 9400841 | 2/1996 | Netherlands | 128/774 |

*Primary Examiner*—Robert L. Nasser
*Attorney, Agent, or Firm*—Rader, Fishman, Grauer & McGarry

[57] ABSTRACT

A device for measuring the intravascular diameter of an anatomical duct has a sheath encasing a catheter. One end of the catheter within the sheath has a sensor with a portion being biased radially outwardly relative to the sheath. Graduated visual indicia are disposed on the catheter near the other end of the sheath. When the sheath is inserted into an anatomical duct, the catheter is urged inwardly so that the sensor extends axially from the sheath and biased radially outwardly until it contacts the interior wall of the duct. At this point, the intravascular diameter can be read directly from the graduated visual indicia on the catheter.

10 Claims, 2 Drawing Sheets

METHOD AND APPARATUS FOR MEASURING THE VASCULAR DIAMETER OF A VESSEL

This application is a continuation of U.S. application Ser. No. 60/006,141 filed Nov. 2, 1996.

BACKGROUND OF THE INVENTION

1. Field of the Invention

This invention relates to a surgical measuring device and, more specifically, to a simple and cost-effective device for measuring the intravascular diameter of an anatomical duct such as a blood vessel.

2. Description of Related Art

Endovascular techniques have become increasingly important to surgeons which require a reasonably accurate measurement of the intravascular diameter of a blood vessel so that proper-sized devices are inserted and released within the blood vessel. An improperly-sized device inserted within a blood vessel may not perform the desired function or, more seriously, cause injury to the patient.

Currently, intravascular ultrasound is used to measure the inner diameter of a blood vessel. However, devices which generate and measure ultrasound signals are expensive and require costly additional technical expertise to operate. Therefore, it is desirable to provide a measuring device which facilitates the measurement of the interior diameter of a blood vessel while further providing a cost-effective method of doing so.

SUMMARY OF THE INVENTION

A simple, yet effective device for measuring the intravascular diameter of an anatomical duct has an elongated, flexible sheath with an open proximal end and an open distal end. The sheath will have an outer diameter which is less than the intravascular diameter. A catheter, longer than the sheath, is received within the sheath, and also has a proximal end and a distal end. The catheter proximal end extends outwardly from the proximal end of the sheath and has graduated visual indicia on it, preferably in the nature of a measuring scale. A sensor extends from the distal end of the catheter, and has a portion which is biased radially outwardly, relative to the sheath. The graduated visual indicia are directly proportional to the distance that the sensor portion moves radially.

When the sheath is inserted into an anatomical duct, and the catheter is moved inwardly relative to the sheath until the sensor portion extends axially from the distal end of the sheath and radially into contact with the interior wall of the duct, the intravascular diameter can be easily read directly from the graduated visual indicia.

Another aspect of the invention includes a method for measuring the intravascular diameter of an anatomical duct. The steps of the method include inserting into the duct an elongated, flexible sheath having an open proximal end and an open distal end, and having an outer diameter less than the intravascular diameter. A catheter is provided which has a distal end, the catheter being longer than the sheath and having graduated visual indicia thereon and a sensor extending from the catheter distal end and having a portion thereof which is biased radially outwardly, the graduated visual indicia being directly proportional to the distance the sensor portion moves radially.

The catheter is urged through the proximal end of the sheath until the sensor portion extends axially from the distal end of the sheath and radially into contact with the interior wall of the duct. In this position, the catheter will display the intravascular diameter which is read directly from the graduated visual indicia.

BRIEF DESCRIPTION OF THE DRAWINGS

The invention will now be described with reference to the drawings wherein.

DESCRIPTION OF THE PREFERRED EMBODIMENTS

Figure 1:
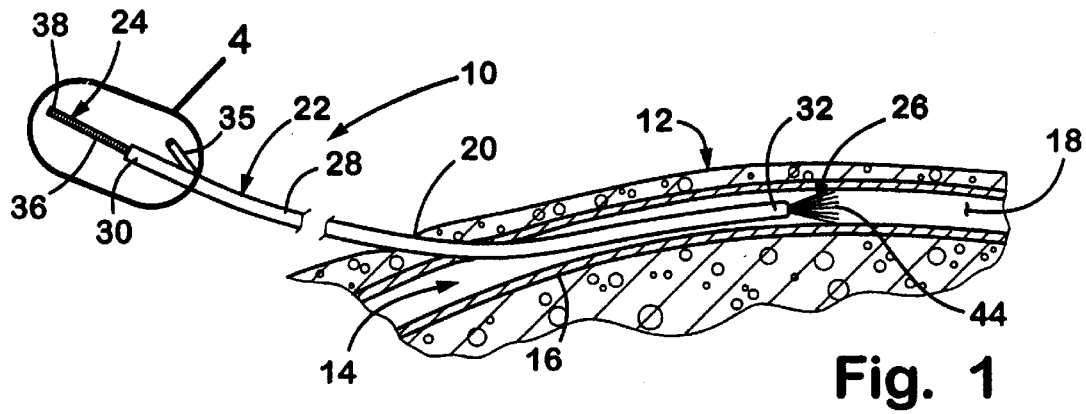
FIG. 1 is a side view of the vascular measuring device in a retracted position according to the invention.
Figure 2:
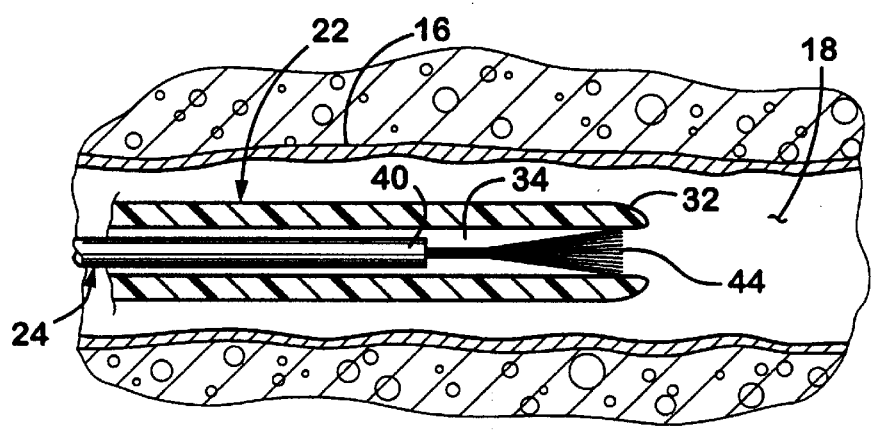
FIG. 2 is a side view of the vascular measuring device of FIG. 1 in an extended position.
Figure 3:
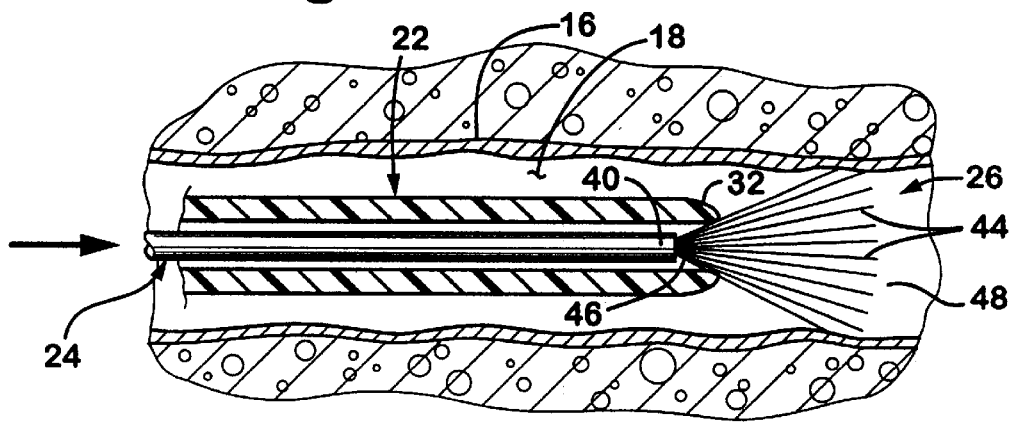
FIG. 3 is a side view of the vascular measuring device of FIG. 1 shown inserted within a blood vessel.

Referring now to the drawings and to FIGS. 1–3 in particular, a vascular measuring device 10 is shown inserted within a patient's body 12. The body 12 includes a blood vessel 14 having a longitudinally-extending annular wall 16 defining an interior chamber 18. The vascular measuring device 10 is shown inserted within an incision or percutaneous puncture 20 made in the body 12 which extends through the wall 16 of the blood vessel 14 and into the blood vessel interior 18. It should be noted that the vascular measuring device 10 of this invention is not limited to a particular type of blood vessel and can be made in various sizes to be compatible with blood vessels of all types and sizes.

The vascular measuring device 10 comprises a sheath 22, a catheter 24 and a sensor 26. The sheath 22 and catheter 24 are constructed of a flexible plastic material with sufficient rigidity to allow the vascular measuring device 10 to be inserted into and pushed along the interiors of blood vessels. The sensor 26 is preferably constructed of a metal alloy which is radiopaque and can also provide tactile sensation at its proximal end when the outer tips of the sensor 26 touch the interior surface of the blood vessel 14. Electronic sensors could also be included in the sensor 26 to provide an audible or visible signal to confirm the contact of the sensor 26 with the blood vessel 14.

The sheath 22 comprises a long, flexible tube 28 having a proximal end 30 and a distal end 32 which surround a central conduit 34. The sheath 22 further includes a side port 35 extending laterally from its proximal end 30 and which is adapted to receive an injected liquid such as dye, saline or other solution as required by the particular medical procedure. The distal end 32 of the catheter 24 includes a tapered tip for easy insertion into a blood vessel.

The catheter 24 comprises a flexible rod 36 having a proximal end 38 and a distal end 40. The rod 36 of the catheter 24 can include a longitudinal central bore (not shown) adapted to receive a wire to assist in steering and guiding the catheter to its desired location within a blood vessel or any other means known to one skilled in the art to assist in guiding a catheter within a blood vessel. The proximal end 38 of the catheter 24 includes several graduated markings 42 (see FIG. 4). The distal end 40 of the catheter 24 mounts the sensor 26. The sensor 26 comprises several radially outwardly-biased filaments 44, each having a proximal end 46 and a distal end 48. The sensor 26 is fully retractable within the sheath 22 and firmly connected to the catheter 24 to prevent accidental dislodgement therefrom. In addition, the distal ends 48 of the filaments 44 are preferably rounded to prevent them from puncturing or penetrating any body tissues.

In assembly, the proximal ends 46 of the filaments 44 are mounted to the distal end 40 of the catheter 24. The catheter 24 is slidably received within the sheath 22 with the proximal end 38 thereof extending axially outwardly of the proximal end 30 of the sheath 22, and the filaments 44 of the sensor 26 within the distal end 32 of the sheath 22. The filaments 44 are thus retained in a retracted position as shown in FIG. 2. The markings 42 are spaced to correspond proportionally to the radial outward movement of the filaments relative to the sheath. Due to their outward bias, the filaments 44 tend to fan outwardly in a conical fashion but are restrained from doing so when they are within the distal end 32 of the sheath 22.

Figure 4:
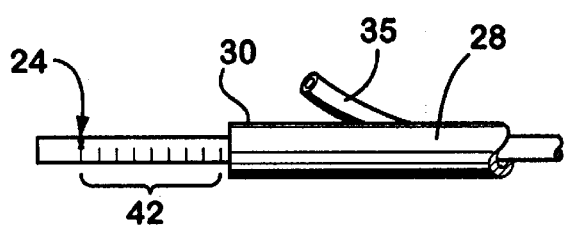
FIG. 4 is an enlarged side view of one end of the vascular measuring device shown in the circular region marked 4 of FIG. 3.

Use of the vascular measuring device 10 to measure the interior diameter of a blood vessel will now be described. Turning now to FIGS. 3 and 4, a surgeon gains access to the blood vessel interior chamber 18 in a conventional manner through the wall 16 of the blood vessel 14. The surgeon inserts the distal end 32 of the sheath 22, carrying the filaments 44 of the sensor 26 in their retracted position, into the incision 20 until the distal end 32 of the sheath 22 enters the interior 18 of the blood vessel 14. The distal end 32 of the sheath 22 is then further urged inwardly through the interior 18 of the blood vessel 14 to the point to be measured, all while the sheath 22 assumes a generally concentrically parallel position within the blood vessel interior 18 with respect to the wall 16. The surgeon then holds the sheath 22 in this position with one hand, while grasping the proximal end 38 of the catheter 24 with the other hand. The proximal end 38 of the catheter 24 is urged axially toward the proximal end 30 of the sheath 22. This action causes the rod 36 of the catheter 24 to move inwardly through the central conduit 34 of the sheath 22. As the rod 36 travels, the distal ends 48 of the filaments 44 exit the distal end 32 of the sheath 22 and extend inwardly within the interior 18 of the blood vessel 14. As the rod 36 continues to move, the outward bias of the filaments urges them to fan outwardly in a conical fashion, such that they will extend radially outwardly of the distal end 32 of the sheath 22 as shown in FIG. 3. As the proximal end 38 of the catheter 24 is urged further inwardly, the filaments 44 will expand radially outwardly to an extent that the distal ends 48 of the filaments 44 abut the interior surface of the blood vessel wall 16. At this point, the surgeon will no longer be able to push the proximal end 38 of the catheter 24 into the sheath 22 due to the resistance of the blood vessel wall 16 against the distal ends 48 of the filaments 44. This can be confirmed by fluoroscopic imaging and/or arteriogram. The surgeon then notes the axial distance that the proximal end 38 has moved inwardly with respect to the proximal end 30 of the sheath 22 by observing the graduated markings 42. The filaments 44 of the sensor 26 are tensioned such that an inward axial movement of a particular distance of the proximal end 38 of the catheter 24 corresponds to an outward radial distance traveled by the distal ends 48 of the filaments 44. For example, if the blood vessel to be measured has an interior diameter of 3 mm, the proximal end 38 of the catheter 24 will be moved axially inwardly a distance of 3 mm. Further, the spring tension of the filaments 44 can be selected to permit a wider scale of graduated markings 42 to be used for easier and more accurate measurements. With properly proportioned indicia on the graduated scale, the inner diameter of the blood vessel can be read directly off the markings.

When the surgeon has completed the measurement of the blood vessel 14, the proximal end 38 of the catheter 24 is pulled outwardly until the filaments 44 are retracted within the central conduit 34 of the sheath 22. The sheath 22 is then withdrawn from the blood vessel 14 through the incision 20 and removed from the body 12.

Figure 5:
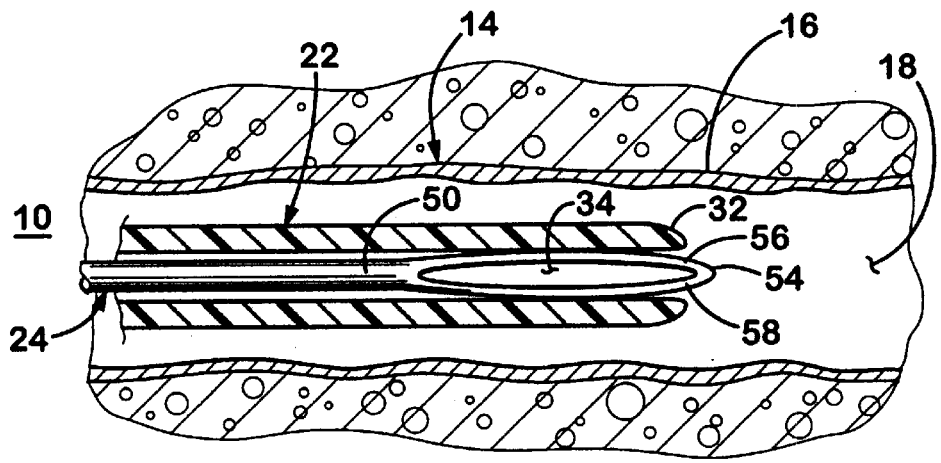
FIG. 5 is a side view of an alternative embodiment of the vascular measuring device in a retracted position according to the invention.
Figure 6:
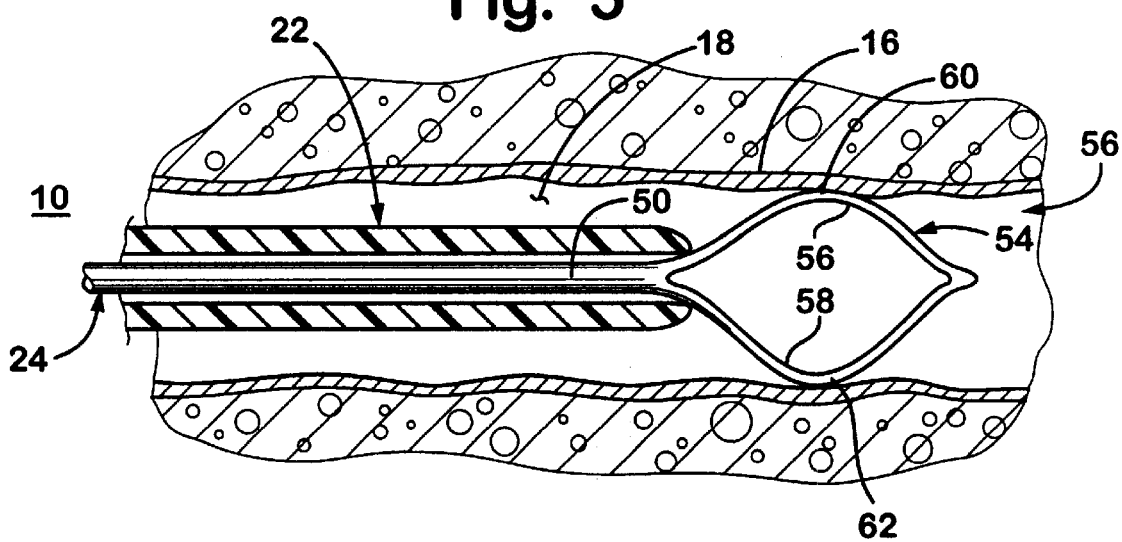
FIG. 6 is a side view of the vascular measuring device of FIG. 5 in an extended position.

Turning now to FIGS. 5–6, an alternative embodiment of the vascular measuring device 10 is shown inserted within an interior 18 of a blood vessel 14 and includes a longitudinal catheter 24 inserted within an annular sheath 22. The catheter 24 comprises a longitudinal rod 50 having graduated markings similar to the first embodiment at its proximal end and a sensor 54 at its distal end. The sensor 54 comprises a pair of outwardly-biased arcuate arm springs 56 and 58 joined together at their forward ends and mounted at their rearward ends to the longitudinal rod 50. As in the previous embodiment, the longitudinal rod 50 of the catheter 24 is slidable between retracted and extended positions relative to the distal end 32 of the sheet 22. When the sensor 54 is in the retracted position within the sheath 22, the interior wall of the sheath 22 retains the arcuate arm springs 56 and 58 in a longitudinally flat position and prevents the arm springs 56 and 58 from bowing outwardly. When the longitudinal rod 50 of the catheter 24 slides forwardly relative to the distal end 32 of the sheath 22 to extend the arm springs 56 and 58 substantially beyond the distal end 32 of the sheath 22, the arm springs 56 and 58 bow laterally outwardly in a convex fashion from the distal end 32 of the sheath 22.

In operation, the sheath 22 carrying the catheter 24 in a retracted position, as shown if FIG. 5, is inserted longitudinally within the interior 18 of a blood vessel 14. When the sheath 22 and catheter 24 are located in a desired position, the longitudinal rod 50 of the catheter 24 may be urged forwardly relative to the sheath 22 until the arm springs 56 and 58 extend laterally outwardly where central outer portions 60 and 62 of the arm springs 56 and 58 contact the blood vessel wall 16. At this point, the longitudinal rod 50 of the catheter 24 will no longer be able to be urged forwardly due to the resistance between the springs 56 and 58 and the blood vessel wall 16. The surgeon can then read the graduated marketings on the catheter 24 to determine the axial movement of the catheter 24 relative to the sheath 22 which corresponds to the outward lateral movement of the central portions 60 and 62 of the arm springs 56 and 58, respectively.

While the invention has been particularly described in connection with certain specific embodiments thereof, it is to be understood that this is by way of illustration and not of limitation, and the scope of the above disclosure should be construed as broadly as the prior art will permit.

I claim:

1. A device for measuring the intravascular diameter of a vessel comprising:
   an elongated, flexible sheath having an open proximal end and an open distal end, and having an outer diameter less than the intravascular diameter;
   a rod longer than the sheath, and received within the sheath, said rod having a proximal end and a distal end, the rod proximal end extending outwardly from the open proximal end of the sheath and having graduated visual indicia thereon; and a sensor extending from the rod distal end, wherein the sensor comprises three or more filaments, each filament biased radially outwardly with respect to the distal end of the sheath, at least one of the at least three filaments not being diametrically opposed to any one of the remaining filaments, and the graduated visual indicia being directly proportional to the distance the filaments move radially;

whereby when the sheath is inserted into the vessel, and the rod moved inwardly relative to the sheath until the filaments extend axially from the distal end of the sheath and radially into contact with the interior wall of the vessel, the intravascular diameter of the vessel can be read directly from the graduated visual indicia.

2. The device of claim 1 further comprising an injection port located adjacent to the open proximal end of the sheath and communicating with the open distal end of the sheath, whereby a liquid can be injected through the injection port to the open distal end of the sheath.

3. A method of measuring the intravascular diameter of a vessel comprising the steps of:

inserting into the vessel an elongated, flexible sheath having an open proximal end and an open distal end, and having an outer diameter less than the intravascular diameter;

providing a rod having a distal end, the rod being longer than the sheath and having graduated visual indicia thereon and a sensor extending from the rod distal end, the sensor comprising three or more filaments, each filament biased radially outwardly with respect to the distal end of the sheath, at least one of the at least three filaments not being diametrically opposed to any one of the remaining filaments, the graduated visual indicia being directly proportional to the distance the filaments move radially;

urging the rod through the proximal end of the sheath until the filaments extend axially from the distal end of the sheath and radially into contact with the interior wall of the vessel; and reading the intravascular diameter directly from the graduated visual indicia.

4. The method of claim 2 further comprising the step of confirming the measurement by:

providing an injection port located adjacent to the open proximal end of the sheath and communicating with the open distal end of the sheath; and injecting a liquid through the injection port to the open distal end of the sheath.

5. A device for measuring the intravascular diameter of a vessel comprising:

an elongated, flexible sheath having an open proximal end and an open distal end, and having an outer diameter less than the intravascular diameter;

a rod longer than the sheath, and received within the sheath, said rod having a proximal end and a distal end, the rod proximal end extending outwardly from the open proximal end of the sheath and having graduated visual indicia thereon;

a sensor extending from the rod distal end and having a portion thereof which is biased radially outwardly, the graduated visual indicia being directly proportional to the distance the sensor portion moves radially; and a protruding injection port located adjacent to the open proximal end of the sheath and communicating with the open distal end of the sheath;

whereby when the sheath is inserted into the vessel, and the rod moved inwardly relative to the sheath until the sensor portion extends axially from the distal end of the sheath and radially into contact with the interior wall of the vessel, the intravascular diameter of the vessel can be read directly from the graduated visual indicia, and a liquid can be injected through the injection port to the open distal end of the sheath.

6. A device for measuring the intravascular diameter of a vessel comprising:

an elongated, flexible sheath having an open proximal end and an open distal end, and having an outer diameter less than the intravascular diameter;

a rod longer than the sheath, and received within the sheath, said rod having a proximal end and a distal end, the rod proximal end extending outwardly from the open proximal end of the sheath and having graduated visual indicia thereon; and a sensor extending from the rod distal end, wherein the sensor comprises outwardly biased spring arms joined at an outer end to each other and at an inner end to the distal end of the rod and to each other, and the graduated visual indicia being directly proportional to the distance the spring arms move radially;

whereby when the sheath is inserted into the vessel, and the rod moved inwardly relative to the sheath until the spring arms extend axially from the distal end of the sheath and radially into contact with the interior wall of the vessel, the intravascular diameter of the vessel can be read directly from the graduated visual indicia.

7. The device of claim 6 further comprising an injection port located adjacent to the open proximal end of the sheath and communicating with the open distal end of the sheath, whereby a liquid can be injected through the injection port to the open distal end of the sheath.

8. A method of measuring the intravascular diameter of a vessel comprising the steps of:

inserting into the vessel an elongated, flexible sheath having an open proximal end, an open distal end, a protruding injection port located adjacent to the open proximal end and communicating with the open distal end, and an outer diameter less than the intravascular diameter;

providing a rod having a distal end, the rod being longer than the sheath and having graduated visual indicia thereon and a sensor extending from the rod distal end and having a portion thereof which is biased radially outwardly, the graduated visual indicia being directly proportional to the distance the sensor portion moves radially;

urging the rod through the proximal end of the sheath until the sensor portion extends axially from the distal end of the sheath and radially into contact with the interior wall of the vessel; and reading the intravascular diameter directly from the graduated visual indicia.

9. A method of measuring the intravascular diameter of a vessel comprising the steps of:

inserting into the vessel an elongated, flexible sheath having an open proximal end and an open distal end, and having an outer diameter less than the intravascular diameter;

providing a rod having a distal end, the rod being longer than the sheath and having graduated visual indicia thereon and a sensor extending from the rod distal end, the sensor having outwardly biased spring arms joined at an outer end to each other and at an inner end to the distal end of the rod and to each other, and the graduated visual indicia being directly proportional to the distance the spring arms move radially;

urging the rod through the proximal end of the sheath until the spring arms extend axially from the distal end of the sheath and radially into contact with the interior wall of the vessel; and reading the intravascular diameter directly from the graduated visual indicia.

10. The method of claim 9 further comprising the step of confirming the measurement by:

providing an injection port located adjacent to the open proximal end of the sheath and communicating with the open distal end of the sheath; and injecting a liquid through the injection port to the open distal end of the sheath.

\* \* \* \* \*